United States Patent [19]
Ryan

[11] Patent Number: 5,088,982
[45] Date of Patent: * Feb. 18, 1992

[54] SAFETY WINGED NEEDLE MEDICAL DEVICES

[75] Inventor: Dana W. Ryan, Franklin, Tenn.

[73] Assignee: Ryan Medical, Inc., Brentwood, Tenn.

[*] Notice: The portion of the term of this patent subsequent to May 8, 2007 has been disclaimed.

[21] Appl. No.: 257,407

[22] Filed: Oct. 13, 1988

Related U.S. Application Data

[63] Continuation-in-part of Ser. No. 162,569, Mar. 1, 1988, Pat. No. 5,059,185, and a continuation-in-part of Ser. No. 224,920, Jul. 27, 1988, Pat. No. 4,923,445.

[51] Int. Cl.$^5$ ............................................. A61M 5/00
[52] U.S. Cl. .................................... 604/110; 604/192; 604/198; 604/263; 128/763
[58] Field of Search ............... 604/110, 162, 177, 192, 604/194–198, 240–243, 363, 111, 181, 185, 187, 188, 199, 211, 212, 214, 216, 232, 234; 128/760, 762–767, 770, DIG. 26

[56] References Cited

U.S. PATENT DOCUMENTS

| | | | |
|---|---|---|---|
| 2,571,683 | 10/1951 | Bastien | 604/198 |
| 2,725,058 | 11/1955 | Rathkey | |
| 3,064,648 | 11/1962 | Bujan | |
| 3,073,306 | 1/1963 | Linder | 106/198 |
| 3,464,581 | 9/1969 | Burke | 604/243 |
| 3,640,275 | 2/1972 | Burke et al. | |
| 3,670,727 | 6/1972 | Reiterman | |
| 3,782,383 | 1/1974 | Thompson et al. | |
| 3,890,971 | 6/1975 | Leeson et al. | 604/198 X |
| 3,969,581 | 9/1969 | Burke | 601/243 |
| 4,015,600 | 4/1977 | Liautaud | |
| 4,170,993 | 10/1979 | Alvarez | 604/198 |
| 4,326,519 | 4/1982 | D'Alo et al. | 604/177 |
| 4,349,022 | 2/1982 | Ishikawa | |
| 4,356,822 | 11/1982 | Winstead et al. | 604/198 |
| 4,366,817 | 1/1983 | Thomas | |
| 4,389,210 | 6/1983 | Genese | 604/177 |
| 4,392,856 | 7/1983 | Lichtenstein | |
| 4,417,887 | 11/1983 | Koshi | 604/192 |
| 4,425,120 | 1/1984 | Sampson et al. | 604/198 |
| 4,573,976 | 3/1986 | Sampson et al. | 604/263 |
| 4,576,671 | 3/1986 | Shimanaka | |
| 4,611,382 | 9/1986 | Clark | |
| 4,627,842 | 12/1986 | Katz | |
| 4,631,097 | 12/1986 | Mitchell | 61/198 |
| 4,643,199 | 2/1987 | Jennings et al. | 604/198 |
| 4,655,751 | 4/1987 | Harbaugh | 604/198 |
| 4,666,435 | 5/1987 | Braginetz | 604/198 |
| 4,681,567 | 7/1962 | Masters et al. | 604/198 |
| 4,690,675 | 9/1987 | Katz | |

(List continued on next page.)

Primary Examiner—David J. Isabella
Assistant Examiner—K. Reichle
Attorney, Agent, or Firm—David P. Gordon

[57] ABSTRACT

Shielded winged needled medical devices which minimize accidental needlesticks of the skin by an exposed contaminated needle are provided. The medical devices include a hollow inner tube having a pair of circumferential grooves on the outside thereof, and a slightly larger hollow winged shield which is slidable relative to the inner tube. Lugs circumferentially spaced about the rearward end of the shield yieldingly engage the rearward groove during use of the medical device and thereby permit normal use of an exposed needle. Thereafter, the shield may be moved relative to the tube along the long axis of the tube to a second position wherein the shield covers the now-contaminated needle. The flexibility of the material of the shield in conjunction with a shoulder on the inner tube body forwardly adjacent a forward circumferential groove permit the medical devices to be assembled. In an unshielded position, relative rotational movement between the inner tube and shield is prevented by providing a shield and inner tube of non-circular cross section, by providing a outwardly extending ratchet teeth on the forward end of the inner tube which engage corresponding inwardly extending teeth in the forward end of the winged outer shield, or by providing rear rotational locking wings on the inner tube which extend through axial slits in the rear of the winged shield.

18 Claims, 3 Drawing Sheets

U.S. PATENT DOCUMENTS

| | | | |
|---|---|---|---|
| 4,702,738 | 10/1987 | Spencer | 604/198 |
| 4,702,739 | 10/1987 | Milerad | 604/198 |
| 4,723,943 | 2/1987 | Spencer | 604/198 |
| 4,737,144 | 4/1988 | Choksi | 604/198 |
| 4,738,603 | 4/1988 | Boyon | 601/198 |
| 4,747,830 | 5/1988 | Glayor et al. | 604/110 |
| 4,747,837 | 5/1988 | Hauck | 604/263 |
| 4,758,231 | 7/1988 | Haber et al. | 604/198 |
| 4,781,692 | 11/1988 | Jagger et al. | 604/171 |
| 4,790,827 | 12/1988 | Haber et al. | 604/198 |
| 4,816,022 | 3/1989 | Poncy | 604/198 |
| 4,820,282 | 4/1989 | Hogan . | |
| 4,906,235 | 3/1990 | Roberts | 604/263 |
| 4,923,445 | 5/1990 | Ryan | 604/198 |

FIG. 1 PRIOR ART
FIG. 2
FIG. 3
FIG. 4
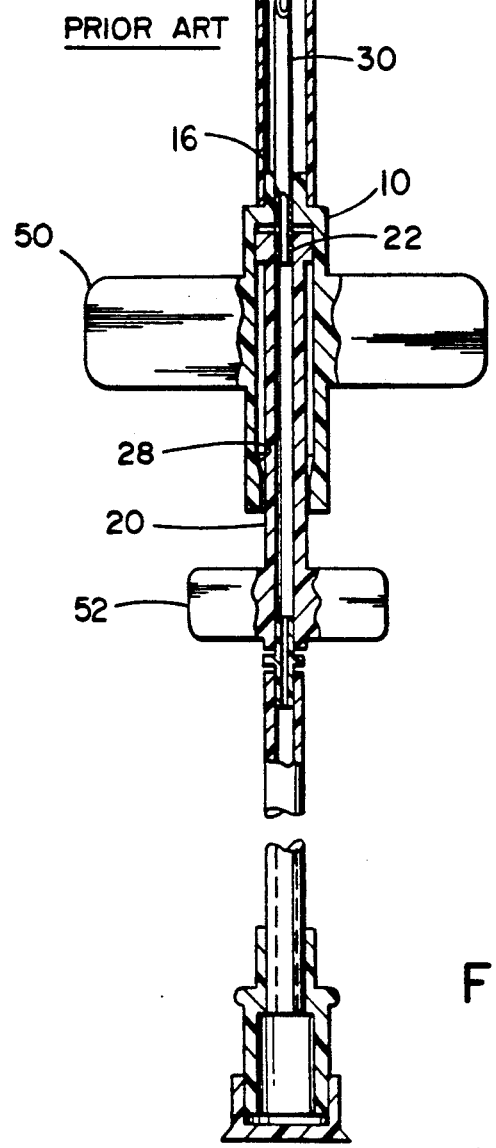
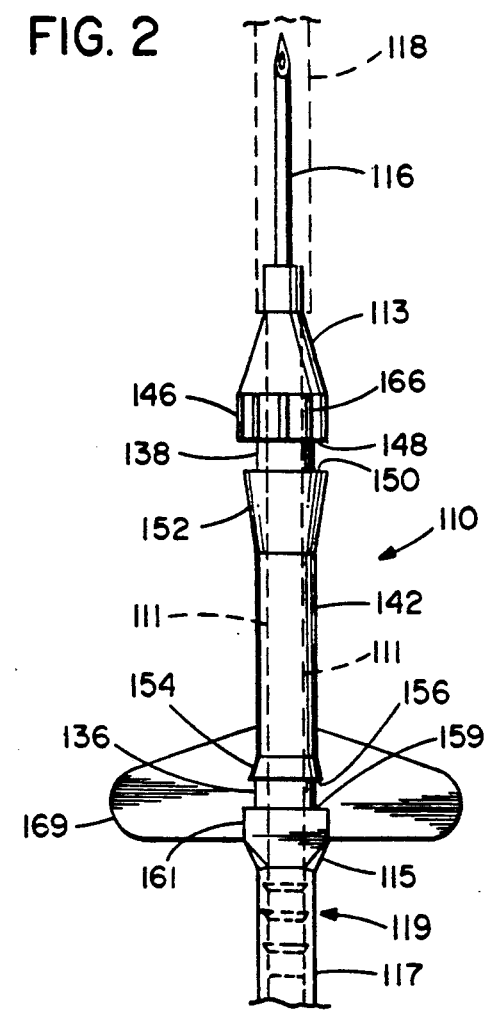
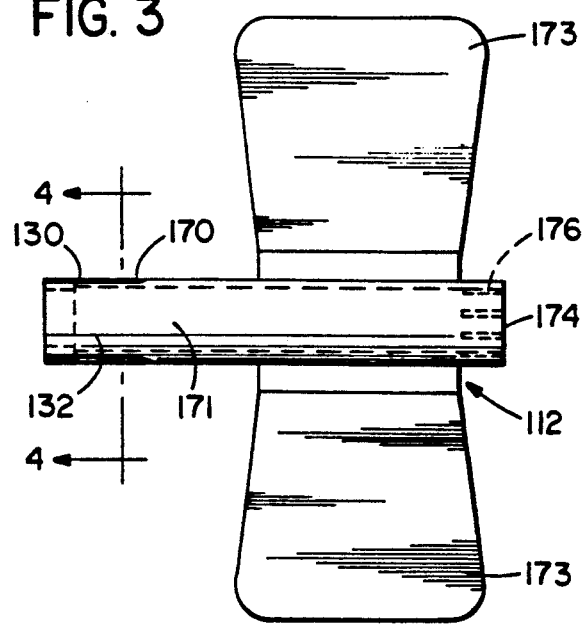
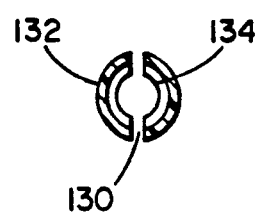

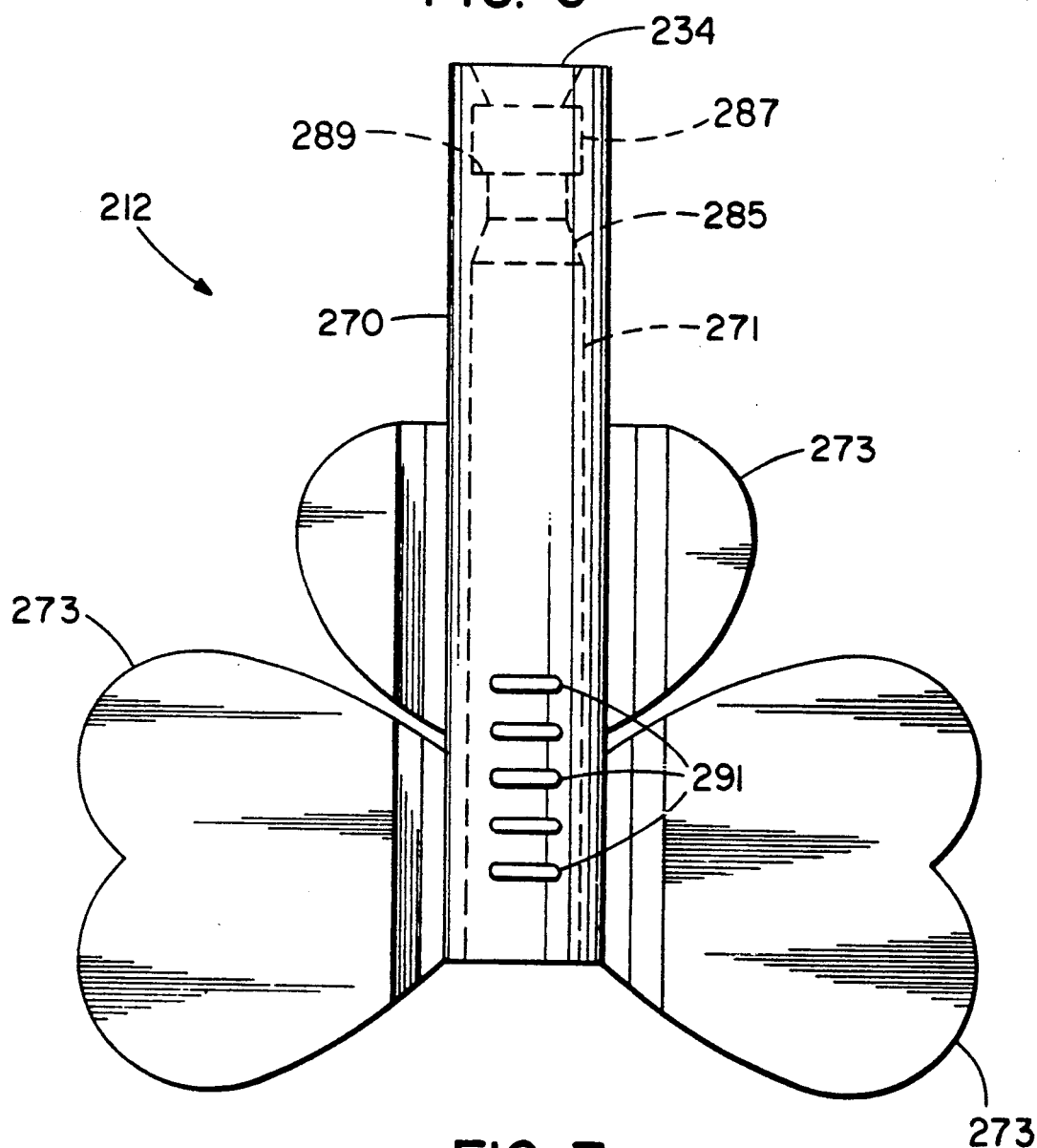
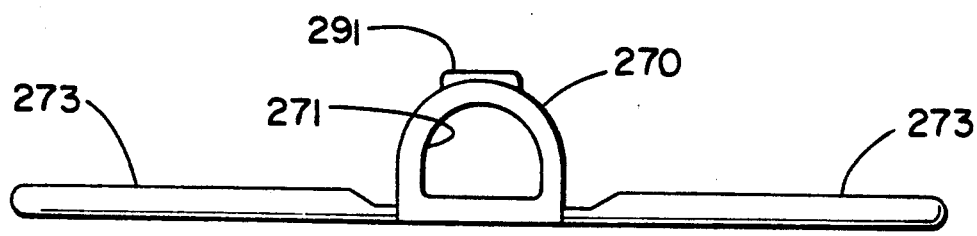

SAFETY WINGED NEEDLE MEDICAL DEVICES

This application is a continuation-in-part of U.S. patent application Ser. Nos. 162,569 and 224,920, respectively filed Mar. 1, 1988 and July 27, 1988, now U.S. Pat. Nos. 5,059,185 and 4,923,445, respectively, which are hereby incorporated by reference herein.

BACKGROUND OF THE INVENTION

The present invention generally relates to winged needle medical devices. More particularly, the present invention relates to safety winged needle medical devices such as winged blood collection needles, winged infusion needles, and blood collection bags with attached winged needles, which are designed to minimize the incidence of accidental needlesticks after needle contamination.

Accidental needlesticks have long been a problem in the medical profession. Accidental needlesticks most often occur during the recapping of a contaminated needle or immediately after use and prior to safe disposal. Such needlesticks place the medical professional (clinician) at risk. When needles are not recapped, additional accidental needlesticks are caused by uncapped needles found in patient beds, linens, and in garbage cans, and place health care, housekeeping and sanitation personnel at risk. Because accidental needlesticks can now result in deadly incurable diseases as well as the previously appreciated serious, but curable diseases, the need for eliminating the needlestick problem has reached extreme urgency. In addressing the urgency, many devices have been proposed. Indeed, reference may be had to the background section of parent application hereof, U.S. patent application Ser. No. 162,569 for a discussion of the prior art of safety needles.

While numerous safety needles of varying complexity and feasibility have been proposed, fewer safety devices for winged needle arrangements have been proposed; perhaps due to the more flexible nature of typical winged needle devices. One proposed safety winged needle device is the retractable safety winged needle of Jagger et al., U.S. Pat. No. 4,676,783. As seen in FIG. 1, herein, the Jagger et al. device includes an outer shield 10, an inner tube 20, a needle 30, wings 50, and tabs 52. The outer shield 10 which has wings 50 attached to it has inner camming surfaces 28 which act as a restriction on one end and a constriction 16 on the needle end. The needle 30 is attached to an enlarged end 22 of the inner tube 20, the other end of which has the tabs 52 attached to it. The device is used by holding the wings 50 while pushing the needle 30 into a vein. Upon removing the needle from the vein, the practitioner pulls back on the tabs 52 attached to the inner tube while holding the wings 50 attached to the outer tube in place. As a result, the inner tube 20 slides backward inside the outer tube 10 until the enlarged end of the inner tube 20 is caught in the inner camming surface 28 of the outer tube 10. At that point, the needle 30 is safely covered by the outer tube 10, and with the inner and outer tubes wedged together, the assembly may be safely disposed.

While the Jagger et al. device is attractive in its simplicity, it apparently has not gained acceptance in the marketplace because it does not provide means to lock or secure the needle and hold it in place during venipuncture. Moreover, it is very difficult to manufacture and assemble. In manufacturing, the enlarged end 22 of the inner tube must eventually be received inside the outer tube 10. However, the camming surfaces 28 of the outer tube 10 prevent such insertion.

SUMMARY OF THE INVENTION

It is therefore and object of the present invention to provide improved winged needle safety devices which are easy and economical to manufacture and assemble.

It is a further object of the invention to provide winged needle safety shielded devices which do not require a substantial change of technique and procedure during use and which utilize a standardized locking mechanism in which the movement of a shield from an unshielded position to a locked shielded position may be accomplished in any easy uniform sliding motion.

In accord, with the objects of the invention, a safety shielded winged needle assembly for blood collection and intravenous infusion is provided and is comprised of two cooperating pieces. A first piece is a hollow inner tube needle adaptor having a front end adapted to have a hollow needle secured thereto and a rear end adapted to have flexible tubing secured thereto. The outer surface of the inner tube member (hereinafter referred to as the "tube" or the "inner tube" member) is configured with a pair of axially spaced circumferential grooves with one of the grooves preferably being formed towards the rearmost end of the tube and the other of the grooves preferably being near the forward end of the tube. The second piece of the safety shielded winged needle assembly is a winged outer safety shield (hereinafter referred to as the "shield", "winged shield" or "outer shield"). The outer shield carries the wings of the device. The outer shield is of slightly larger cross-section than the inner tube and during assembly is slidable over the tube. One end of the outer shield has at least one inwardly extending protrusion such that the end may take any of the forms shown in parent U.S. patent application Ser. No. 224,920.

Prior to use of the safety winged needle assembly, the inward protrusions of the shield yieldingly engage the rearmost groove of the inner tube thereby allowing the needle to be exposed and permitting normal use of the winged needle device. Thereafter, the needle may be withdrawn from the vein by sliding the inner tube backwards relative to the shield with the shield in place. In moving the inner tube relative to the outer shield, the shield's protrusion disengages from the rearmost groove and slides along the inner tube until a protrusion engages the forward groove. In such a position, the shield extends over the needle and prevents accidental contact with the contaminated needle. Rotation of the outer tube relative to the inner tube when the shield is in its retracted position and the needle is exposed is eliminated by any of several means. Interlocking ratchet means on the outside of the inner tube and the inside of the outer tube and/or rear locking wings on the inner tube which can engage the coaxial slits in the rear of the outer shield may be provided to eliminate relative rotation. Alternatively, the shield and the inner tube may be shaped as semicircles, half ovals, or other non-circular shapes to prevent rotation.

A better understanding of the safety winged needle medical assembly of the invention, and additional advantages and objects of the invention will become apparent to those skilled in the art upon reference to the detailed description and accompanying drawings.

BRIEF DESCRIPTION OF THE DRAWINGS

FIG. 1 is a plan view of a prior art safety winged needle device;

FIG. 2 is a plan view of the inner tube needle adaptor assembly of a first embodiment of the invention;

FIG. 3 is a plan view of the winged shield of the first embodiment of the invention;

FIG. 4 is a sectional view of a portion of the winged shield of FIG. 2, taken along line 4-4 of FIG. 3;

FIG. 6 is a plan view of the winged shield of the second embodiment of the invention; and FIG. 7 is a sectional view of a portion of the winged shield of FIG. 6 taken along line 7—7 of FIG. 6.

DETAILED DESCRIPTION OF THE PREFERRED EMBODIMENT

Figure 5A:
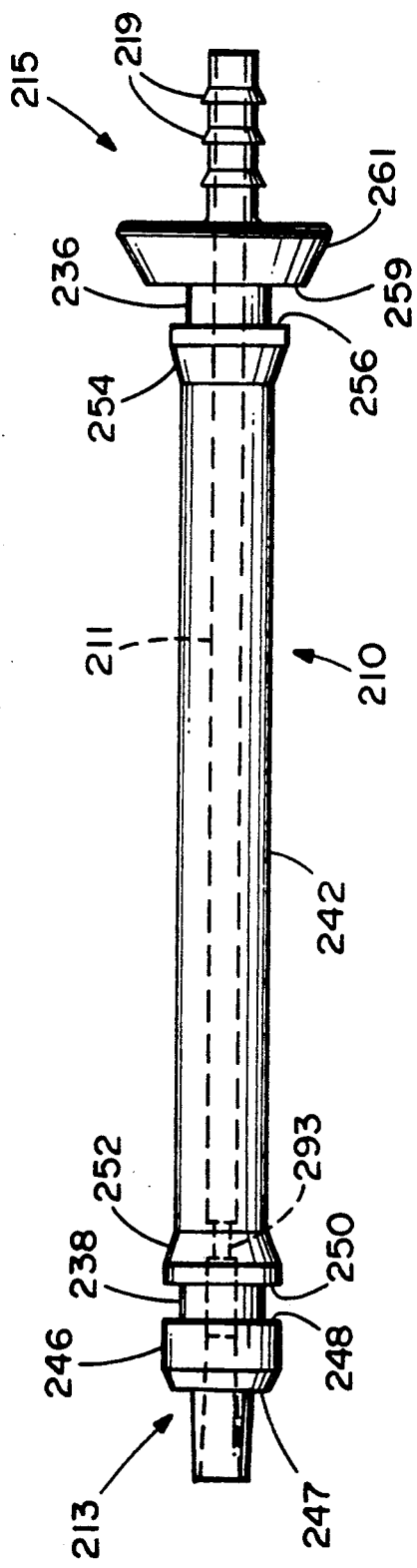
FIGS. 5a and 5b are top and side views respectively of the inner tube needle adaptor assembly of a second embodiment of the invention.

As seen in the FIGS. 2-4, the safety winged needle devices of the first embodiment of the invention are generally comprised of two pieces: a hollow inner tube needle adaptor 110; and an outer winged shield 112. Both pieces are typically made of molded plastic, although other materials are acceptable. As seen in FIG. 2, the inner tube needle adaptor 110 which has a preferably uniform hollow passage therethrough (denoted by dashed lines 111), is adapted at its front end 113 to accept and hold a standard hollow infusion or collection needle 116. Thus, a portion of the front end 113 of the inner tube 110 has an inner hollow which preferably matches the diameter of the non-piercing end of the needle, and glue is used along with a friction fit to hold the needle in place relative to adaptor assembly 110. A standard needle cover 118 may be placed over the needle 116 and may attach to front end 113 by a friction fit.

The rear end 115 of inner tube needle adaptor 110 is adapted to mate with and hold a standard tubing 117 which is used for blood collection and intravenous infusion assemblies. Preferably, the outer diameter of a portion of rear end 115 is arranged to be slightly smaller than the inner diameter of the tubing 117. Ring ridges 119 are provided around the outside of the mating portion of the rear end 115 and together with glue act to prevent the tubing 117 from sliding off the rear end of needle adaptor assembly 110.

One important aspect of the invention is the precise geometry of the outer wall 142 of the inner tube 110. Circumferential grooves 136 and 138 are formed in wall 142, with rear end 115 adjacent rear groove 136 and front end 113 adjacent front groove 138. At the junction of forward end 113 and forward groove 138, a shoulder 146 is formed. From the shoulder 146, the forward end 113 tapers down such that it can receive needle 116 and needle cover 118. The rearward extension of shoulder 146 forms the forwardmost ledge 148 of circumferential groove 138. The rearmost ledge 150 of groove 138 has a slightly smaller diameter than that of shoulder 146 (for assembly purposes as will be described hereinafter), and as wall 142 extends rearward from ledge 150, its outside diameter gradually decreases to form a sloped wall portion or ramp generally illustrated as 152. Thereafter, the wall 142 is of constant diameter until it reaches ramp 154 which terminates in the forwardmost ledge 156 of circumferential groove 136. The rearmost ledge 159 of rear circumferential groove 136 is also the forward extension of shoulder 161 of the rear section 115. Shoulder 161 is preferably of greater diameter than the forward ledge 156 of groove 136 to prevent shield 112 (as will be described in greater detail hereinafter) from sliding backward off of inner tube 110. From shoulder 161, the rear end 115 of inner tube 110 gradually tapers down to a diameter which is suitable for mating with tubing 117.

The inner tube 110 as shown in FIG. 2 preferably includes two additional features, each of which in conjunction with corresponding features on the winged shield 112 is capable of preventing rotation of the inner tube 110 relative to the outer winged shield 112 while the needle 118 is unshielded (i.e. during insertion and use of the needle). A first feature is the notches or grooves (also referred to as ratchet teeth) 166 which are formed in shoulder portion 146 of forward end 113. The ratchet teeth extend outwardly from the inner tube 110 and are arranged to mesh and lock with inwardly extending ratchet teeth 176 of the winged shield 112. The second feature is the rear rotational locking wings 169 which extend outwardly from the inner tube 110 around the rear groove area. Wings 169 are designed to extend into slots 130 in the rear of the winged shield 112 and to thereby prevent rotation of inner tube 110 relative to outer shield 112 when so engaged. Rear rotational locking wings 169 also serve to provide a surface onto which a medical practitioner may grasp so as to pull inner tube 110 backward until needle 116 is withdrawn from the patient and shielded by shield 112.

Turning to FIGS. 3 and 4, the winged shield 112 of the first embodiment of the invention is seen. Winged shield 112 is generally a cylindrical member having an outside wall 170 and an inner wall 171 (indicated by dashed lines), with standard wings 173 extending therefrom. Wings 173, which are integrally molded with the shield, are flexible as in the standard winged assemblies so as to permit the entire assembly (needle adaptor 110; winged shield 112; and needle 116) to be manipulated carefully. Wings 173 are also used as a surface from which to attach the needled blood collection or intravenous infusion assembly onto the patient such as by taping or suturing.

In the first embodiment of the invention, the front end of winged shield 112 preferably includes ratchet teeth 176 which extend radially inwardly and are arranged to lock with outwardly extending ratchet teeth 166 of the inner tube 110 so as to prevent rotation of the shield 112 relative to the inner tube 110. Rachet teeth 166 may extend completely around the inner circumference, or may be in selected locations as desired. The middle section of winged shield 112 provides a surface from which the wings 173 may extend. The rear section of winged shield 112 has a plurality of circumferentially spaced axial slots or slits 130, preferably sized to easily engage locking wings 169 of inner tube 110 and to prevent rotation of inner tube 110 relative to winged shield 112. Slots 130 in cylindrical shield 112 cause the rear section of the shield to assume the form of slightly flexible tabs 132. Formed on the inner surface of tabs 132 and integral therewith are a plurality of protrusions or lug members 134 which extend radially inwardly from each of the tabs 132. Lug members 134 are adapted to yieldingly engage circumferential groove 136 of the inner tube 110 to thereby maintain the shield 112 in a retracted position (i.e. not covering needle 116). The tabs 132 are sufficiently flexible to permit the lug members to be forced out of groove 136 and to permit the shield 112 to be moved forward manually to an extended position (i.e. covering needle 116). As will be described hereinafter, the construction of the shield 112 and inner tube 110 are such that the shield 112, when in the extended locked position with lug members 134 locked into groove 138, is extremely difficult to remove from the inner tube 110, while during assembly, the shield 112 is slipped over tube 10 without lug members 134 locking into groove 138.

Upon assembly of a safety winged needle device according to the first embodiment of the invention, the rear end of winged shield 112 is forced over the shoulder 146 of the inner tube 110. The lug member 134 attached to tabs 132 initially contact forward end 113 as forward end 113 tapers outward toward shoulder 138, thereby forcing flexible tabs 132 outward. As the lug members 134 pass over and by raised shoulder 146 (having ratchet teeth 166 thereon) they instantaneously remain spread, both due to the contraction time required to reassume an unstressed position and due to the position assumed with the tabs 132 angling outwardly, such that they can be quickly moved past groove 138 without falling into groove 138. As the shield 112 is pushed rearwardly over the inner tube 110, the lug members 134 press against ramp 152 which is of decreasing diameter, i.e., the tabs 132 are no longer flexed outwardly as a result of the reduced diameter of wall 142. The lug members 134 ultimately pass over ramp 154 on inner tube 110 and fall into rear circumferential groove 136 where they are temporarily captured. Because rear end 115 of inner tube 110 has shoulder 161, lugs 134 of shield 112 cannot continue rearwardly past groove 136. Also, because of ledge 156, lug members 134 will not disengage in a forward direction without the application of force.

Where inner tube 110 includes rear rotational locking wings 169, the rear wings 169 must be aligned to extend into slots 130 of shield 112 during assembly. Thus, as lug member 134 pass over ramp 154, the slots 130 and rear wings 169 are aligned to permit wings 169 to enter slots 130. Upon lug members 134 entering circumferential groove 136, not only is shield 112 fixed in position in an axial direction relative to inner tube 110, but rotation of shield 112 relative to tube 110 is eliminated. Where inner tube 110 includes outwardly extending ratchet teeth 166 and winged shield 112 includes inwardly extending ratchet teeth 176, rotation of the shield 112 relative to the tube 110 is likewise eliminated while lug members 134 are engaged in groove 136.

With winged shield 112 assembled over inner tube 110, the needle 116 may be attached to forward end 113 of inner tube 110, needle cover 118 placed there-over, and the flexible tubing 117 may be attached to the rear end 115 of inner tube 110. Of course, if desired, such attachments may be accomplished prior to assembly of winged shield 112 over inner tube 110.

In use, the practitioner chooses a blood collection or IV infusion assembly having a needle of the desired size and length. The winged needled assembly includes the inner tube 110 with attached needle 116 covered by needle cover 118, the winged shield 112 engaged with tube 110 in an unshielded position (i.e. lugs 134 in groove 136), and tubing 117 extending from the rear end 115 of inner tube 110. The practitioner removes the needle cover 118. Squeezing wings 173 of winged shield 112 together and gripping the shield 112 together with the inner tube 110, the practitioner inserts needle 116 into the vein of the patient. Upon proper insertion, the practitioner releases the wings 173 and shield 112, and preferably either tapes or sutures the wings 173 to the skin of the patient to prevent movement of the needle upon movement of the patient. If blood is to be collected in a container system (not shown), tubing 117 is connected to the container system in a well-known manner, thereby providing gravity feed with which to draw blood through needle 116, inner tube 110, tubing 117 and into the container. Similarly, if blood is to be collected into a vacuum tube (i.e. a blood collection vacuum tube, not shown), the tube is attached to the flexible tubing 117 via adaptors well known in the art. Or, if blood, or another liquid is to be intravenously administered to a patient via a bag or container (not shown), the tubing 117 is coupled in a well-known manner to a liquid container which is placed above the level of the needle 116 to provide positive pressure and to assure the flow of the liquid though tubing 117, inner tube 110, and needle 116 into the patient (not shown).

Upon completion of the blood collection or intravenous infusion, the practitioner may remove the needle from the patient and shield the needle in either of two manners. In one sequence, the practitioner removes the needle from the patient by gripping rear rotational locking wings 169 and pulling backward on the wings 169 while holding the wings 173 of shield 112 in place. Because tabs 132 on shield 112 are flexible, lug members 134 which are not deeply seated in circumferential groove 136 are pulled out of groove 136 over ledge 156. As tube 110 is pulled backward, lug members 134 contact ramp 154, wall 142, and then ramp 152. When the lug members 134 contact ramp 152 in a direction in which the diameter of wall 142 of inner tube 110 is increasing, increased friction and tension are provided on lugs members 134. Thus, when lug members 134 eventually fall into circumferential groove 138, they preferably make an audible click, providing a positive indication of locking beyond the visual indication. Because of its depth and because of the increased diameter of raised shoulder 146, groove 138 retains the lug members 134 of the shield 112. It is difficult to remove the shield once it is locked into circumferential groove 138, and a positive lock is assured, protecting medical personnel and others against injuries from the contaminated needle. The wings 173 are then detached from the patient, and the entire assembly is safely discarded in accord with established procedures.

A second sequence for removing and shielding the needle is for the practitioner to remove the tape or sutures holding the wings 173 on the patient. The needle is then removed from the patient by pulling back on the entire assembly (tube 110 and shield 112). Once the needle is removed, shielding is obtained by moving the winged shield 112 forward relative to the inner tube 110 (as opposed to pulling tube 110 back into shield 112). Regardless, the interaction of the lug members 134 with the grooves 136 and 138, ramps 154 and 152, and outer surface 142 of tube 110 remains substantially the same, such that the shield is eventually locked over the needle 116 by lug members 134 being locked in groove 138.

Figure 5B:
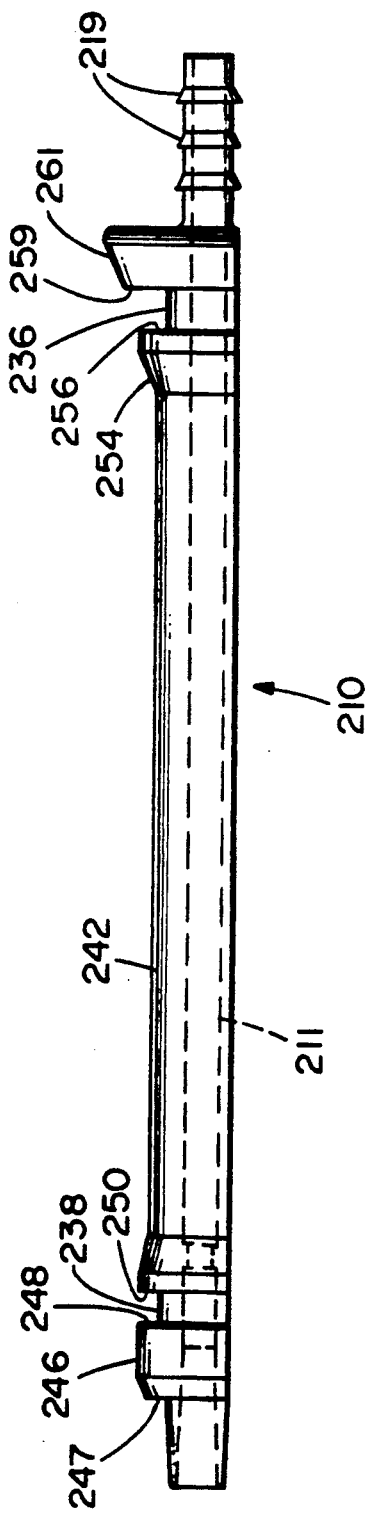

Turning to FIGS. 5-7, a second embodiment of the invention is seen with inner tube 210 and outer shield 212 (parts of FIGS. 5-7 corresponding to parts of FIGS. 2-4 having corresponding numbers displaced by 100). Thus, as seen in FIGS. 5a and 5b, inner tube 210 has a hollow passage 211 and a front end 213 adapted to accept and hold a standard hollow infusion or collection needle (not shown). In fact, the opening in front end 213 tapers slightly such that glue may be inserted around the needle and wicked backwardly. Also, as seen in FIG. 5a, a throat 293 in the hollow front end 113 limits the backward movement of the needle. The rear end 215 of inner tube 210 is adapted to mate with and hold a standard tubing (not shown), and ring ridges 219 are provided to accomplish the same. If desired, the needle may be caused to angle downward relative to a horizontal defined by the skin of the patient. This angling, which is preferably small (generally less than ten degrees) is accomplished either by angling the opening in hollow front end, or by providing a wedge 9 (shows is phantom) on shield 212 either on the bottom of surface 270, or on wings 273. The angled needle aids in the venipuncture procedure and reduces trauma to the vein upon needle removal.

As in the first embodiment, the inner tube 210 has an outer wall 242 having circumferential (albeit semicircular) grooves 236 and 238. However, unlike the first embodiment, the outer wall 242 is not circular in shape, but is preferably shaped as half an oval so as to fit into similarly shaped outer shield 212 (the shape of which is seen in FIG. 7). Forward of front groove 238 is a shoulder 246. The rearward extension of shoulder 246 forms the forwardmost ledge 248 of circumferential groove 238. For purposes of assembly (as aforedescribed with reference to FIGS. 2-4), the rearmost ledge 250 of groove 238 has a slightly smaller diameter than that of shoulder 246. As wall 242 extends rearward from ledge 240, its outside diameter gradually decreases to form a sloped wall portion or ramp generally illustrated as 252. Thereafter, the wall 242 is preferably of constant diameter until it reaches ramp 254 which terminates in the forwardmost ledge 256 of circumferential groove 236. The rearmost ledge 259 of rear groove 236 is also the forward extension of wing shoulder 261. Wing shoulder 261 serves the double purpose of preventing the shield 212 from sliding backward off of inner tube 210, and providing a surface which may be grasped by a practitioner in pulling the needle and inner tube assembly out of a vein and into the protected shielded position.

Turning to FIGS. 6 and 7, the winged shield 212 of the second embodiment is seen to have an outer wall 270 and inner wall 271 in the half-oval shape, with wings 273 in the form of a shamrock extending therefrom. The advantage of the half-oval shape is that rotation of the inner tube relative to the outer shield is eliminated without the necessity of ratchet teeth or a wing-slot arrangement. Moreover, the flat surface of the shield may be placed on the skin surface of the patient, thereby providing more surface contact for comfort, and a better angle for needle insertion. Of course, other shapes such as a semicircle, triangle, etc. can also provide both advantages, and both advantages can also be provided where the shield and inner tube do not assume the same shape. However, half-oval or semicircular inner tubes and shields are believed to be optimal due to their advantages and ease of manufacture. On the other hand, the shamrock shape of the wings 273 is primarily stylistic.

Besides the circumferential shape of the shield which eliminates relative rotation without the use of ratchet teeth and/or the wing/slot arrangement, the FIG. 6 embodiment of the outer shield differs from the shield of FIG. 3 in several ways. A first difference is the inclusion of ribs 291 extending from the outer surface of the shield. Ribs 291 permit the practitioner with the use only of a single hand to shield an exposed needle. The practitioner would accomplish shielding by gripping the inner tube with up to four fingers and then using the thumb to push on the ribs of the shield. The added friction provided by ribs 291 to the thumb permits the forward thrust of the thumb to force protrusion 234 out of rear groove 236. In fact, a practitioner, using only a single hand, should preferably be able to cause the shield to assume the fully shielded position with protrusion 234 of the shield locked in groove 238 of the inner tube.

A second difference between the shields of the FIG. 3 and FIG. 6 embodiments is the protrusion arrangement at the rear end of the winged shields. As seen in FIG. 6, protrusion 234 corresponding to protrusion 134 of FIG. 3 is provided. However, in addition, the inner surface 271 of winged shield 212 includes a ramped section 285, followed by indent 287 (preferably at the same diameter of most of inner surface 271), followed by the wedge-shaped protrusion 234. The provided arrangement corresponds closely in an inverse manner to the front end 213 of the inner tube 210 which includes shoulder 246 which fits into indent 287 and groove 238 which accepts protrusion 234. In the extended shielded position, with protrusion 234 engaged in groove 238, the leading edge 247 of shoulder 246 of the inner tube abuts the rear edge 289 of ramp 285 of the shield and provides extra stability and assurance that the winged shield will not pull off and leave the contaminated needle exposed.

One of the reasons that the inner surface 271 of shield 212 at its rear end can be shaped in a manner corresponding to the front end of inner tube 210 is the elimination of the ratchet mechanism on the inner tube 210. However, if a ratchet mechanism was desirable, it should be appreciated that the rear end of winged shield 212 can be arranged according to the teachings of parent U.S. patent application Ser. No. 224,920 to provide additional stability.

In assembling the safety winged needle device of FIG. 6, protrusion 234 will engage shoulder 246 of inner tube 210. Because protrusion 234 is preferably wedge-shaped, the expansion of the rear end of shield 212 is more gradual (although the assembly is accomplished in milliseconds) and helps protect the integrity of the shield. Because of the speed of assembly, the wedge-shape of the protrusion 234, and the engagement of ramp with shoulder 246, after protrusion 234 passes shoulder 246 it does not lock in groove 238, but rather engages ramp 252. After sliding over the outer surface 242 of the inner tube, the protrusion 234 engages ramp 254 and then engages circumferential groove 236 where the unshielded position is assumed. After the blood collection or infusion has been completed, shielding is accomplished in either of the manners discussed relative to FIG. 3. Of course, if the needle is withdrawn from the vein prior to shielding, the ribs 291 on the winged shield preferably permit the practitioner to accomplish shielding with the use of only a single hand.

There has been described and illustrated herein safety winged needle devices for use in blood collection and intravenous infusion. While particular embodiments of the invention have been described, it is not intended that the invention be limited thereby, as it is intended that the invention be broad in scope. Thus, for example, while the invention was described as essentially comprising two unitary pieces, it will be appreciated that several pieces could be utilized to form either the tube or the shield. Moreover, while the wall of the tube is preferably formed with a ramp to cause the shield to "click" when the protrusion or lugs of the shield snap into the circumferential groove of the tube, it will be appreciated that the ramp is not essential to the invention. Indeed, for winged needle devices where it is desired that the withdrawal of the needle from the vein be coincident with the shielding of the needle by the shield, it may not always be desirable to have to provide additional force on the inner tube (via rear wings, rear shoulder, or flexible tubing attached to the rear of the inner tube) to force the lugs of the shield over such a ramp. Further, while the locations of the grooves in the inner tube of the assembly were described as being at the forward and rear ends of the inner tube, those skilled in the art will appreciate that the exact location is not critical provided the contaminated needle is shielded by the shield after use. Similarly, the shapes of the forward and rear sections of the inner tube are not critical, provided they are arranged to mate respectively with the needle and flexible tubing, and provided they function to appropriately lock the lug members (protrusions) of the winged shield in the circumferential grooves and permit proper movement of the lug members during assembly.

It should further be understood that while certain terminology such as "circumferential" was used in describing the grooves on the inner tube, such terminology is intended to be broad in scope to encompass a groove in the circumference regardless of the circumferential shape, and it is not intended that the invention be limited to circular geometries. Moreover, while particular embodiments with particular features were disclosed, it should be appreciated that various of the features could be utilized in conjunction with any of the embodiments. For example, the ribs of FIG. 6 could be utilized with the winged shield of FIG. 3. Likewise, the protrusion arrangements of the parent U.S. patent application Ser. No. 224,920 could be used with both of the instant embodiments. Therefore, it will be apparent to those skilled in the art that yet other changes and modifications may be made to the invention as described without departing from the scope of the invention as so claimed.

I claim:

1. A medical device for assembly with a hollow needle, comprising:
    a) an inner tube member having
        a passageway therethrough,
        a front end adapted to have the hollow needle secured thereto,
        a rear end adapted to receive at least one of a fluid conduit means and a fluid container means, and
        an outer surface having first and second circumferential grooves, said first groove being rearward of said second groove, wherein said outer surface of said tube member subscribes a larger cross-section area through said inner tube member at the forward end of said second circumferential groove than at the rearward end of said second circumferential groove; and
    b) a resiliently flexible hollow outer winged shield member having
        an inner surface subscribing a slightly larger cross-section than said outer surface of said inner tube member,
        a front end having an opening therein,
        an open rear end, and
        at least one protrusion extending inwardly from said inner surface of said hollow outer member, the inner surface of said at least one protrusion subscribing a smaller cross-section than said outer surface of said inner tube member at the forward end of said second circumferential groove of said inner tube member, said at least one protrusion engaging said first circumferential groove to maintain said shield member in a first retracted position in which the hollow needle is exposed, and engaging said second circumferential groove to maintain said shield member in a second extended position in which the needle is covered by said shield member, wherein said at least one protrusion is disengageable from said first circumferential groove and said shield member is slidable relative to said inner tube member between said first position and said second position.

2. A medical device according to claim 1, wherein:
said outer surface of said inner tube member has a ramp adjacently rearward of said second circumferential groove such that cross-sections through said inner tube member subscribe increasing areas in a direction approaching said second circumferential groove, and
said at least one protrusion slidably engages said outer surface of said tube member such that when engaging said ramp in moving from said first position to said second position, additional tension is placed on said at least one protrusion and additional resistance to movement is obtained.

3. A medical device according to claim 2, wherein:
said outer surface of said tube member includes an enlarged portion rearward of said first circumferential groove, said enlarged portion having a cross-section subscribing an area larger in diameter than a cross-sectional area through said tube member at the forward end of said first circumferential groove.

4. A medical device according to claim 3, wherein:
said inner surface of said winged shield member is substantially cylindrical,
said open rear end of said hollow outer winged shield member has at least two slots along longitudinal axes parallel to a long axis of said winged shield member, said slots causing said at least one inner protrusion to form inwardly extending lugs; and
said inner tube member further includes at least one substantially flat rear rotational locking wing extending generally radially from said tube member, said rear rotational locking wing extending through and locking with one of said at least two slots in said outer winged shield member when said inwardly extending lugs of said outer winged shield member are engaged in said first circumferential groove thereby preventing said outer winged shield member from rotating relative to said inner tube member when said shield member is in said first retracted position.

5. A medical device according to claim 4, wherein:
said tube member further comprises on its outer surface first locking means; and
said hollow outer winged shield member comprises on its inner surface second locking means,
said first and second locking means adapted to lock so as to prevent rotational motion of said outer winged shield member relative to said tube member when said inwardly extending lugs of said outer winged shield member are engaged in said first circumferential groove.

6. A medical device according to claim 5, wherein:
said second locking means comprises a plurality of ratchet teeth radially extending inwardly from said inner surface of said hollow outer winged shield member; and
said first locking means comprises a plurality of ratchet teeth radially extending outwardly from said outer surface of said innter tube member.

7. A medical device according to claim 1, wherein:
said inner surface of said winged shield member is substantially cylindrical,
said open rear end of said hollow outer winged shield member has at least two slots along longitudinal axes parallel to a long axis of said winged shield member, said slots causing said at least one inner protrusion to form inwardly extending lugs; and
said inner tube member further includes at least one substantially flat rear rotational locking wing extending generally radially from said tube member, said rear rotational locking wing extending through and locking with one of said at least two slots in said outer winged shield member when said inwardly extending lugs of said outer winged shield member are engaged in said first circumferential groove thereby preventing said outer winged shield member from rotating relative to said inner tube member when said shield member is in said first retracted position.

8. A medical device according to claim 1, wherein:
said inner surface of said winged shield member is substantially cylindrical,
said tube member further comprises on its outer surface first locking means; and
said hollow outer winged shield member comprises on its inner surface second locking means,
said first and second locking means adapted to lock so as to prevent rotational motion of said outer winged shield member relative to said tube member when said at least one inwardly extending protrusion of said outer winged shield member is engaged in said first circumferential groove.

9. A medical device according to claim 8, wherein:
said second locking means comprises a plurality of ratchet teeth radially extending inwardly from said inner surface of said hollow outer winged shield member; and
said first locking means comprises a plurality of ratchet teeth radially extending outwardly from said outer surface of said inner tube member.

10. A medical device according to claim 1, wherein:
at least one of said outer surface of said inner tube member and said inner surface of said outer winged shield member is substantially non-cylindrical in shape to prevent relative rotation therebetween.

11. A medical device according to claim 10, for use on a patient, wherein:
said outer winged shield member includes an outer surface having a substantially flat portion running along substantially the entire longitudinal length of said outer winged shield member for placement adjacent the skin of the patient.

12. A medical device according to claim 11, wherein:
a cross-section through said inner surface of said outer winged shield member has a shape chosen from one of semi-circle, and a truncated oval.

13. A medical device according to claim 11, wherein:
at least one of said front end of said inner tube member and said outer winged shield member includes means for causing said hollow needle to assume an angle of less than ten degrees relative to a horizontal defined by the skin of the patient to which said winged shield member is attached.

14. A medical device according to claim 2, wherein:
said outer surface of said inner tube member further includes a shoulder section adjacently forward said second circumferential groove, said shoulder section of relatively constant diameter along an axis parallel to the longitudinal axis of said inner tube member, and
said inner surface of said winged shield member further includes a ramped section terminating in a recessed section which in turn terminates at said rear end of said winged shield member in said at least one protrusion, wherein said recessed section is arranged to reciprocate with said shoulder section of said inner tube member such that the forward end of said shoulder section abuts the termination of said ramped section of said winged shield member when said at least one protrusion is locked in said second circumferential groove in said extended position of said winged shield member.

15. A medical device according to claim 14, wherein:
said inner surface of said shield member is of substantially uniform diameter forward said ramped section of said inner surface of said shield member,
the area subscribed by said inner surface of said recessed section of said rear of said winged shield member is substantially equal to the area subscribed by the inner surface of the substantially uniform section of said winged shield member.

16. A medical device according to claim 14 for use on a patient, wherein:
said outer winged shield member has an outer surface with a substantially flat surface for placement adjacent the skin of the patient, and
said inner surface of said winged shield member and said outer surface of said inner tube member are of substantially the same over-all shape, with a cross-section through said inner surface of said outer winged shield member arranged to be a shape chosen from one of semi-circle, and a truncated oval.

17. A medical device according to claim 16, wherein said outer winged shield member includes a plurality ribs extending outwardly from the outer surface of said outer winged shield member.

18. A medical device according to claim 1, wherein:
said outer winged shield member includes an outer surface with a substantially flat surface for placement adjacent the skin of the patient to which said winged shield member is attached, and at least one of said front end of said inner tube member and said winged shield member includes means for causing said hollow needle to assume an angle of less than ten degrees horizontal defined by the skin of the patient to which said winged shield member is attached.

* * * * *